(12) United States Patent
Goodwin

(10) Patent No.: US 7,487,688 B2
(45) Date of Patent: Feb. 10, 2009

(54) SAMPLING PORTS AND RELATED CONTAINER SYSTEMS

(75) Inventor: Michael E. Goodwin, Logan, UT (US)

(73) Assignee: Hyclone Laboratories, Inc., Logan, UT (US)

( * ) Notice: Subject to any disclaimer, the term of this patent is extended or adjusted under 35 U.S.C. 154(b) by 383 days.

(21) Appl. No.: 11/385,626

(22) Filed: Mar. 20, 2006

(65) Prior Publication Data

US 2007/0214899 A1 Sep. 20, 2007

(51) Int. Cl.
*G01N 1/10* (2006.01)
(52) U.S. Cl. .................. 73/863.81; 73/864.73; 374/141
(58) Field of Classification Search ............... 73/863.81, 73/864.73; 374/141
See application file for complete search history.

(56) References Cited

U.S. PATENT DOCUMENTS

| | | | | |
|---|---|---|---|---|
| 2,516,097 | A | * | 7/1950 | Volpi et al. ............... 73/863.31 |
| 3,085,435 | A | * | 4/1963 | Miscoe et al. ......... 73/863.81 X |
| 3,144,676 | A | | 8/1964 | Mura |
| 4,327,726 | A | | 5/1982 | Kwong et al. |
| 4,594,903 | A | * | 6/1986 | Johnson ............... 73/863.81 X |
| 5,085,087 | A | * | 2/1992 | Franck et al. ............ 73/864.73 |
| 5,565,015 | A | | 10/1996 | Kobayashi |
| 6,071,005 | A | | 6/2000 | Ekambaram et al. |
| 6,083,587 | A | | 7/2000 | Smith et al. |
| 6,186,932 | B1 | | 2/2001 | Vallot |
| 6,245,555 | B1 | | 6/2001 | Curtis |
| 6,432,698 | B1 | | 8/2002 | Gaugler et al. |
| 6,494,613 | B2 | | 12/2002 | Terentiev |
| 6,598,474 | B2 | * | 7/2003 | Purpura et al. ............. 73/290 V |
| 6,670,171 | B2 | | 12/2003 | Carll |
| 6,923,567 | B2 | | 8/2005 | Bibbo et al. |
| 7,337,683 | B2 | * | 3/2008 | DeFriez et al. ........... 73/863.23 |
| 2002/0131654 | A1 | | 9/2002 | Smith et al. |
| 2003/0077466 | A1 | | 4/2003 | Smith et al. |
| 2005/0239199 | A1 | | 10/2005 | Kunas et al. |
| 2006/0196501 | A1 | * | 9/2006 | Bibbo et al. ........... 128/200.23 |
| 2006/0240546 | A1 | * | 10/2006 | Goodwin et al. ......... 435/289.1 |

FOREIGN PATENT DOCUMENTS

| | | |
|---|---|---|
| EP | 0 343 885 A1 | 11/1989 |
| EP | 1 602 715 A3 | 12/2005 |
| SU | 473082 A * | 9/1975 |
| WO | WO 2005/068059 A1 | 7/2005 |

* cited by examiner

*Primary Examiner*—Thomas P Noland
(74) *Attorney, Agent, or Firm*—Workman Nydegger

(57) ABSTRACT

A sampling port includes an elongated flexible support tube having an interior surface bounding a first passageway extending between a first end and an opposing second end, the first passageway being closed at the first end of the support tube and open at the second end of the support tube. An elongated flexible sampling tube has an interior surface bounding a second passageway extending between a first end and an opposing second end, the second passageway being open at the first end of the sampling tube, at least a portion of the sampling tube adjacently extending along the length of the support tube and being connected to the support tube. A flange encircles and radially outwardly projecting from the support tube and the sampling tube at a location spaced apart from the first end of the support tube and the first end of the sampling tube.

13 Claims, 10 Drawing Sheets

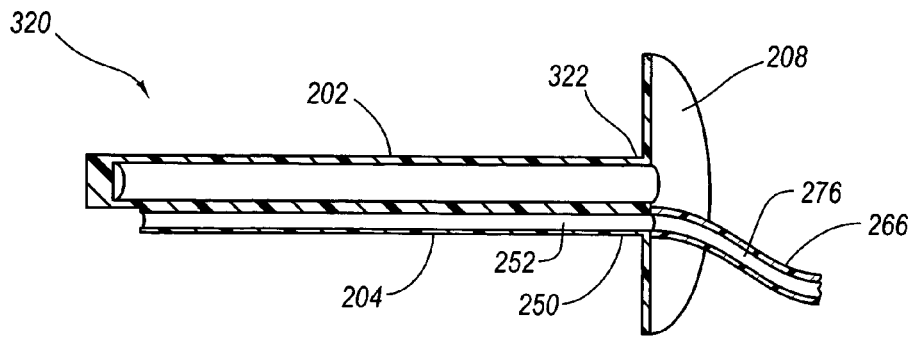
FIG. 12
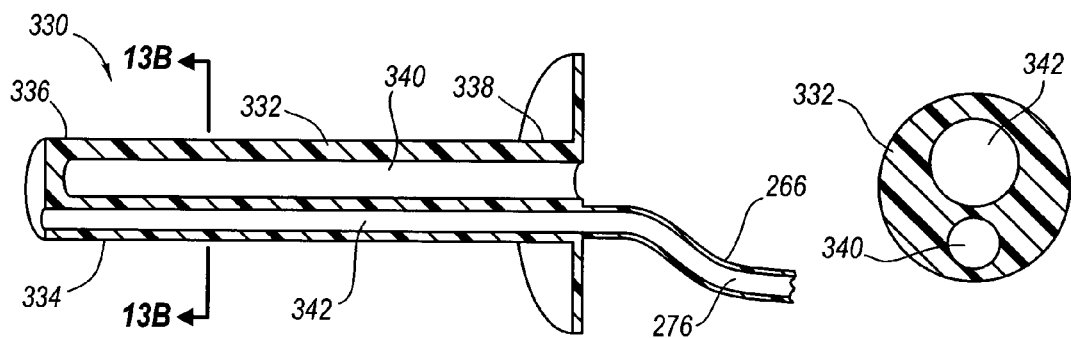 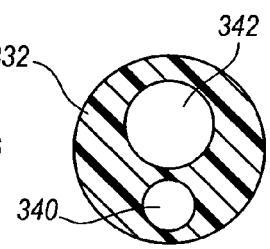
FIG. 13A      FIG. 13B
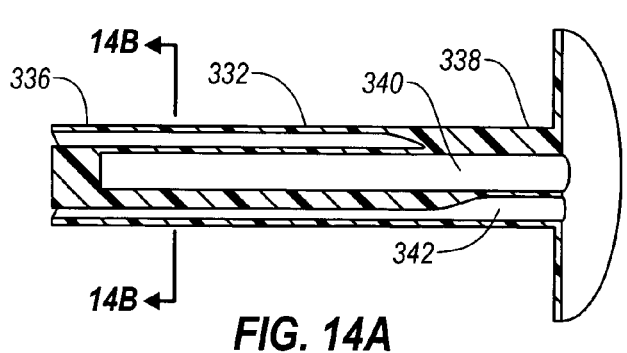 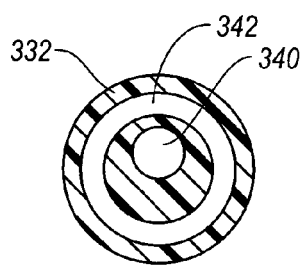
FIG. 14A      FIG. 14B

SAMPLING PORTS AND RELATED CONTAINER SYSTEMS

CROSS-REFERENCE TO RELATED APPLICATIONS

Not applicable.

BACKGROUND OF THE INVENTION

1. The Field of the Invention

The present invention relates to tube ports and sampling ports, and container systems that incorporate such ports.

2. The Relevant Technology

Ports are a necessary feature of bioreactors for delivering controlled volumes of gas, liquid, or other material to growth media containing cells; for extracting matter out of the bioreactor; and for inserting probes, such as a temperature probe, to monitor conditions within the bioreactor. Conventional ports comprise tubular metal or hard plastic stems that are permanently attachable to the bioreactor container. Various tubes or probes are then attached to the ports or are passed through the ports. In all embodiments, great care is taken so that no leaking or contamination occurs at the ports.

Although conventional ports are useful for their intended purpose as detailed above, they have a number of shortcomings. For example, because conventional ports typically are made of metal or hard plastic, the ports are typically rigid and inflexible. Because of this inflexibility, it can be difficult to establish a seal around tubes or other structures that are passed through the ports. As a result, an unwanted dead space can be formed between the ports and the structures passing therethrough.

Furthermore, the inflexibility of conventional ports can cause problems when used with flexible containers. An advantage of using flexible containers is that the containers can be folded up for transport or storage when not in use, making the stored containers more compact, easier to handle, and requiring less room to store. Rigid ports decrease the flexibility of the containers and increase the risk that the ports could damage the containers when the containers are folded around the ports.

Sampling from bioreactors typically occurs by simply connecting a sampling tube to a corresponding port and withdrawing the sample therefrom. This sampling technique typically withdraws the sample fluid from the perimeter of the container. Such a sample, however, may be misrepresentative of the typically more homogeneous fluid that is contained close to the center of the container.

Accordingly, what are needed are improved ports that overcome one or more of the above problems or other shortcomings known in the art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 12 is a cross sectional side view of another alternative embodiment of a sampling port;

FIG. 13A is a cross sectional side view of yet another alternative embodiment of a sampling port;

FIG. 13B is a cross sectional end view of the sampling port shown in FIG. 13a taking along a line defined by 13B-13B;

FIG. 14A is a cross sectional side view of yet another alternative embodiment of a sampling port;

FIG. 14B is a cross sectional end view of the sampling port shown in FIG. 14A taking along a line defined by 14B-14B.

DETAILED DESCRIPTION OF THE PREFERRED EMBODIMENTS

The present invention relates to tube ports and sampling ports as well as container systems that incorporate such ports. In general, the tube ports of the present invention include a flexible tubular stem with a flange encircling and radially outwardly projecting from the stem. The sampling ports of the present invention include an elongated flexible support tube and an elongated flexible sampling tube each coupled together at a mounting location on a body. A flange encircles and radially outwardly projects from the support tube and the sampling tube.

The inventive tube ports and sampling ports can be used in bioreactors where it is necessary to mount probes, delivery and remove growth media and other components, and conduct sampling. However, the inventive tube ports and sampling ports can also be used in fermentation systems and other fluid processing, transport, and/or storage systems or the like.

As a result of using a flexible, tubular stem and flange, select embodiments of the inventive tube ports have a variety of unique benefits over conventional rigid tube ports. By way of example and not by limitation, the inventive tube ports are relatively inexpensive to make and are very flexible, allowing them to be used more easily with flexible containers. For example, due to the flexibility of the tube ports, the tube ports can be connected to flexible bags and other structures using methods and systems that cannot be used with rigid tube ports. The tube ports can also be easily scaled for use in small laboratory experiments or large scale commercial production systems.

The inventive tube ports can be formed as part of a flexible container, such as a disposable bag or liner, or can be coupled to such flexible containers. The tube ports and related container can then be simultaneously sterilized and sold as a unitary system. This approach simplifies the sterilization process. Furthermore, the entire tube port is designed to be soft and flexible so that the combined tube port and container can be folded and/or rolled into a compact shape for storage and/or transport without risk of damage to the tube port or container. Numerous other advantages of different embodiments of the present invention will be discussed below or will be apparent from the following disclosure and appended drawings.

Figure 1:
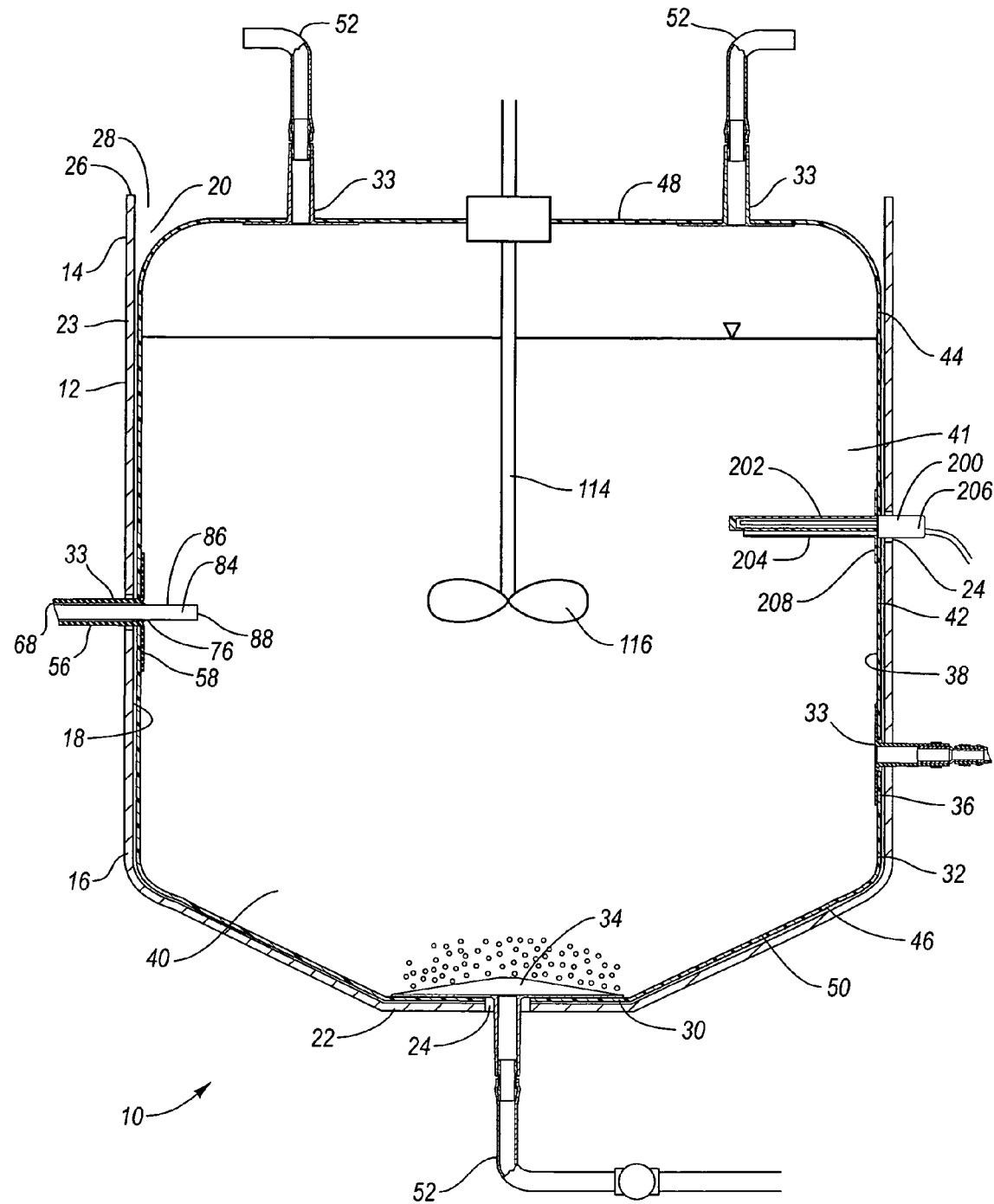
FIG. 1 is a cross sectional side view of a containment system having multiple tube ports and a sampling port.

Depicted in FIG. 1 is one embodiment of a containment system 10 incorporating features of the present invention. Containment system 10 comprises a substantially rigid support housing 12 in which a container system 30 is disposed. Support housing 12 has an upper end 14, a lower end 16, and an interior surface 18 that bounds a compartment 20. Formed at lower end 16 is a floor 22 and sidewalls 23 extend up from floor 22 toward upper end 14. One or more openings 24 can extend through floor 22 or sidewall 23 of container system 30 so as to communicate with compartment 20. Upper end 14 terminates at a lip 26 that bounds an access opening 28 to compartment 20. If desired, a cover, not shown, can be mounted on upper end 14 so as to cover access opening 28. It is appreciated that support housing 12 can come in a variety of different sizes, shapes, and configurations. For example, in one alternative embodiment access opening 28 can be closed by a permanent top end wall. An access port can be formed at another location on support housing 12 such as the sidewall or floor. The access port can be selectively closed by a door.

As also depicted in FIG. 1, container system 30 is at least partially disposed within compartment 20 of support housing 12. Container system 30 comprises a container 32 having one or more tube ports 33 which will be described in more detail below. In the embodiment depicted container 32 comprises a flexible bag-like body 36 having an interior surface 38 that bounds a chamber 40 suitable for holding a fluid 41 or other type of material. More specifically, body 36 comprises a side wall 42 that, when body 36 is unfolded, has a substantially circular or polygonal transverse cross section that extends between a first end 44 and an opposing second end 46. First end 44 terminates at a top end wall 48 while second end 46 terminates at a bottom end wall 50.

Body 36 is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different material that can be separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are each hereby incorporated by specific reference.

In one embodiment, body 36 comprises a two-dimensional pillow style bag wherein two sheets of material are placed in overlapping relation and the two sheets are bounded together at their peripheries to form internal chamber 40. Alternatively, a single sheet of material can be folded over and seamed around the periphery to form internal chamber 40. In another embodiment, body 36 can be formed from a continuous tubular extrusion of polymeric material that is cut to length and the ends seamed closed.

In still other embodiments, body 36 can comprise a three-dimensional bag that not only has an annular side wall but also a two-dimensional top end wall 48 and a two-dimensional bottom end wall 50. Three-dimensional body 36 comprises a plurality of discrete panels, typically three or more, and more commonly four or six. Each panel is substantially identical and comprises a portion of the side wall, top end wall, and bottom end wall of body 36. Corresponding perimeter edges of each panel are seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

It is appreciated that body 36 can be manufactured to have virtually any desired size, shape, and configuration. For example, body 36 can be formed having chamber 40 sized to 10 liters, 30 liters, 100 liters, 250 liters, 500 liters, 750 liters, 1,000 liters, 1,500 liters, 3,000 liters, 5,000 liters, 10,000 liters or other desired volumes. Although body 36 can be any shape, in one embodiment body 36 is specifically configured to be complementary or substantially complementary to compartment 20 of support housing 12.

In any embodiment, however, it is desirable that when body 36 is received within compartment 20, body 36 is uniformly supported by support housing 12. Having at least generally uniform support of body 36 by support housing 12 helps to preclude failure of body 36 by hydraulic forces applied to body 36 when filled with fluid.

Although in the above discussed embodiment container 32 has a flexible, bag-like configuration, in alternative embodiments it is appreciated that container 32 can comprise any form of collapsible container or semi-rigid container. Furthermore, in contrast to having a closed top end wall 48, container 32 can comprise an open top liner. Container 14 can also be transparent or opaque and can have ultraviolet light inhibitors incorporated therein.

Mounted on side walls 42 and top end wall 48 are a plurality of tube ports 33 which are in fluid communication with chamber 40. Although four tube ports 33 are shown, it is appreciated that one, two, three, or more tube ports 33 can be present depending on the intended use of container 32. As such, each tube port 33 can serve a different purpose depending on the type of processing to be undertaken. For example, tube ports 33 can be coupled with a tube, such as fluid line 52, for dispensing fluid or other components into chamber 40 or withdrawing fluid from chamber 40. In addition, such as when container 32 is used as a bioreactor for growing cells or microorganisms, tube ports 33 can be used to provide various probes such as temperature probes, pH probes, dissolved oxygen probes, and the like, access to chamber 40.

Figure 2:
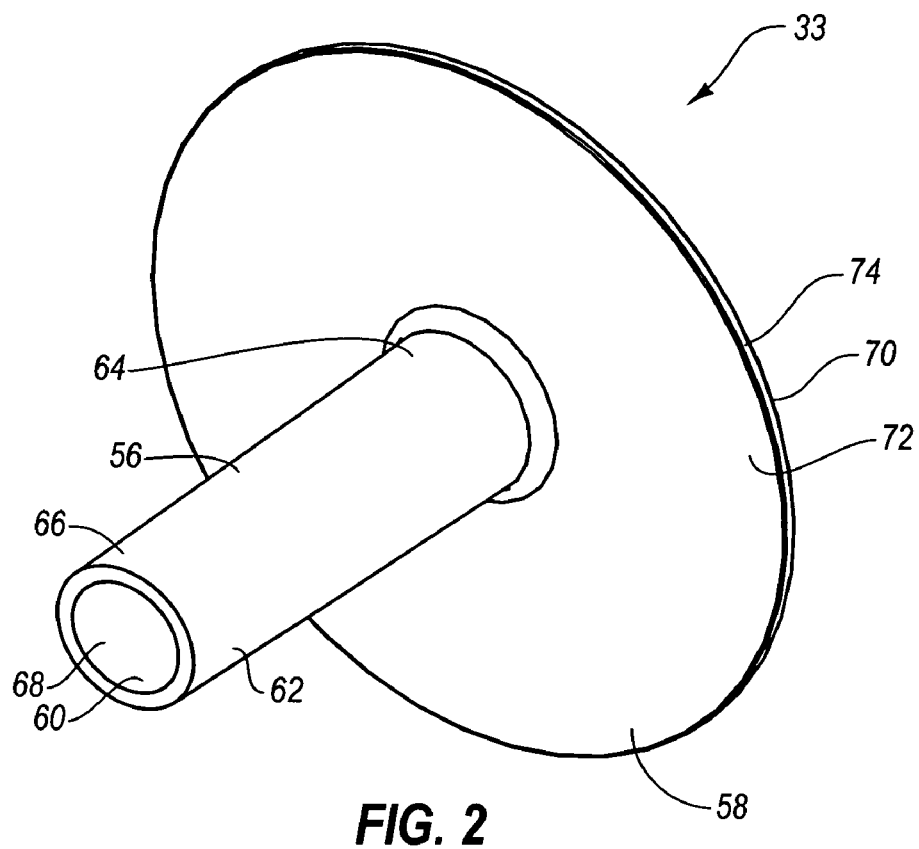
FIG. 2 is a perspective view of one of the tube ports of the containment system depicted in FIG. 1.

In general, each tube port 33 comprises a tubular stem 56 with a flange 58 encircling and radially outwardly projecting from tubular stem 56. Turning to FIG. 2, stem 56 of tube port 33 has an interior surface 60 and an opposing exterior surface 62 each extending between a first end 64 and a longitudinally spaced apart second end 66. Interior surface 60 bounds a passage 68 that longitudinally extends through stem 56. Interior surface 60 and/or exterior surface 62 can contain barbs or other protrusions extending therefrom or, as in the embodiment depicted, can be substantially smooth. One or both of interior surface 60 and exterior surface 62 can also have a constricting taper extending along the length thereof.

Flange 58 encircles stem 56 at first end 64 and radially outwardly projects therefrom. In the embodiment depicted, flange 58 has a substantially circular configuration. In alternative embodiments, flange 58 can be any other desired shape such as elliptical, square, or other polygonal or irregular configurations. Flange 58 has a first side 70 and an opposing second side 72 that each extend out to a perimeter edge 74.

Stem 56 and flange 58 can be molded as a unitary integral piece. Alternatively, stem 56 can be connected to flange 58 by welding using conventional welding techniques such as heat welding, RF energy, ultrasonic, and the like or by using adhesives other any other conventional attaching or fastening techniques.

Figure 3:
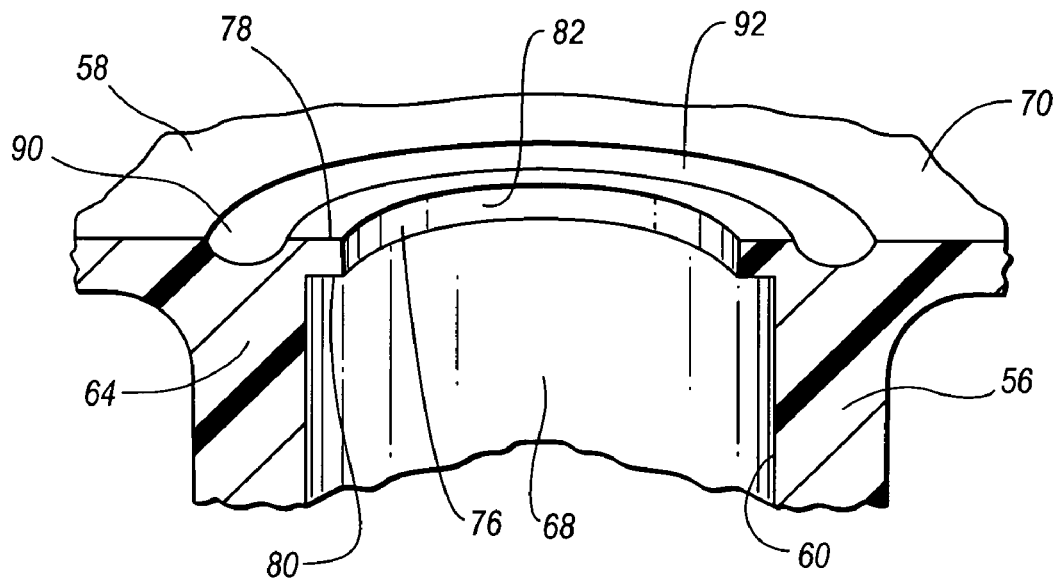
FIG. 3 is a cross sectional side view of a portion of the tube port shown in FIG. 2, showing an annular lip seal.

Turning to FIG. 3, in one embodiment, an annular lip seal 76 radially inwardly projects from interior surface 60 of stem 56 so as to extend into passage 68. Lip seal 76 is comprised of a first sidewall 78 and an opposing second sidewall 80 that extend from interior surface 60 to an interior face 82. Although lip seal 76 can be disposed anywhere along interior surface 60, in the depicted embodiment lip seal 76 is disposed at first end 64 of stem 56 such that flange 58 and lip seal 76 are disposed in substantially the same plane. Furthermore, first side 70 of flange 58 and first sidewall 78 of lip seal 76 are disposed in substantially the same plane. Lip seal 76 is resiliently flexible so as to form an annular seal around a tube, probe, or other device to be inserted through passage 68, thereby preventing fluid or other materials from entering or escaping chamber 40 of container 32 through passage 68.

Figure 4:
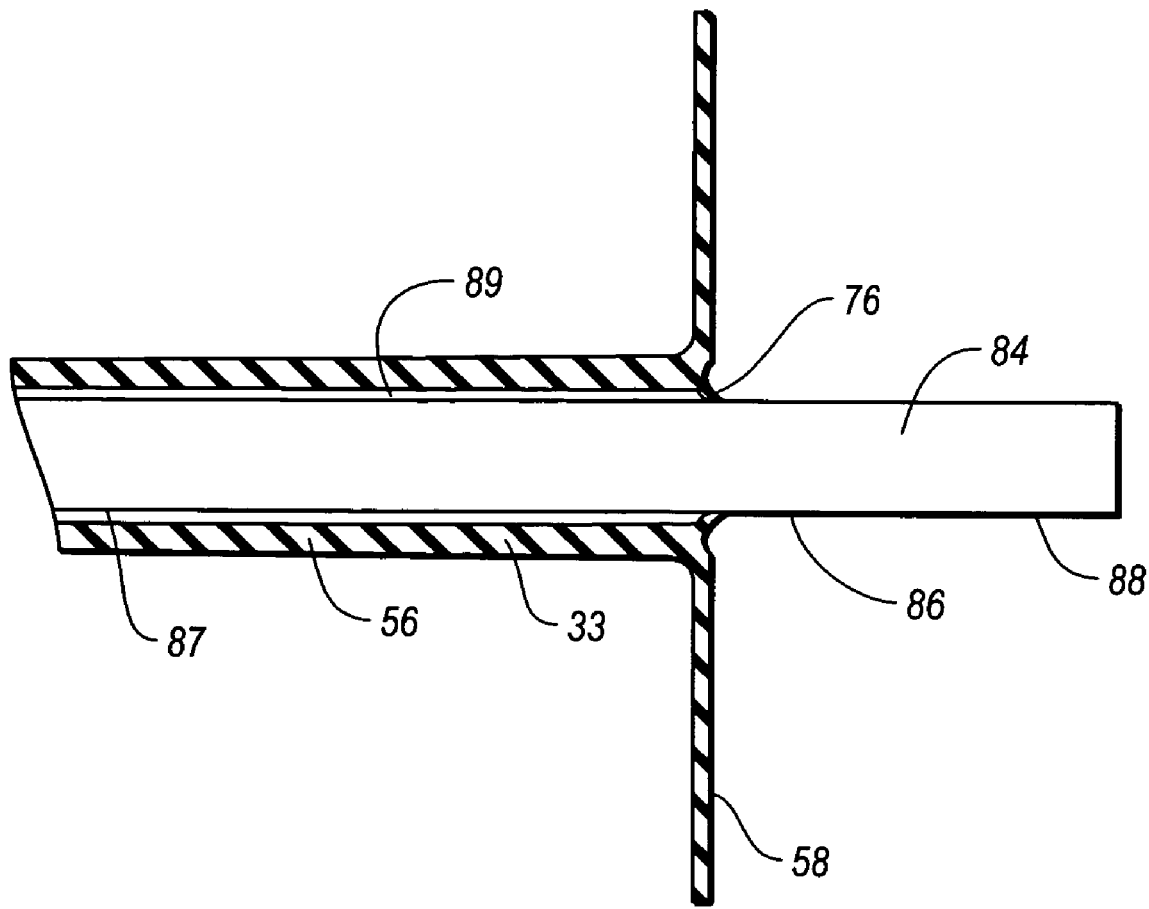
FIG. 4 is a cross sectional side view of the tube port shown in FIG. 2 with a temperature probe inserted therein.

For example, depicted in FIGS. 1 and 4 is a probe 84 having a substantially cylindrical exterior surface 86 extending between a proximal end 87 and an opposing distal end 88. Probe 84 can comprise a dissolved oxygen probe or any other type of probe such as a pH probe, temperature probe, or the like. Prior to filling container 32 with a fluid, distal end 88 of probe 84 is advanced through tubular stem 56 of tube port 33 and past lip seal 76 so that distal end 88 projects freely into chamber 40 of container 32. As probe 84 passes lip seal 76, lip seal 76 outwardly flexes so as to resiliently bias against exterior surface 86 probe 84. As a result, a sealed engagement is formed between lip seal 76 and exterior surface 86 probe 84. This sealed engagement prevents any fluid or other material from entering or existing chamber 40 through tubular stem 66. It thus prevents any material from being caught in a dead space 89 formed between probe 84 and the interior surface of stem 56.

The foregoing embodiment has the advantage that probe 84 can be easily attached to container 32 by sealed engagement and can be easily removed for subsequent sterilization and reuse. In turn, container 32 can be disposed of after a single use so as to minimize cleaning and sterilization. It is appreciated that a variety of other sealing and connecting structures can also be used in connecting probe 84 to tube port 33 and container 32 so as to ensure that probe 84 is sterile when entering container 32. Examples of such connection systems are disclosed in U.S. patent application Ser. No. 11/112,834 that was previously incorporated herein by specific reference.

Returning to FIG. 3, when flange 58 and lip seal 76 are disposed in substantially the same plane, an annular channel 90 can be recessed on flange 58 to aid in the flexibility of lip seal 76. Channel 90 is bounded by a substantially c-shaped floor 92 that is recessed into first side 70 of flange 58 so as to encircle lip seal 76 and the opening to passage 68. That is, channel 90 has an inside diameter that is slightly larger that the inside diameter of passage 68 at first end 64 of stem 56. Channel 90 decreases the surrounding support of lip seal 76 so that lip seal 76 can more easily flex as probe 84 or other structure is passed therethrough.

Lip seal 76 is comprised of a soft, flexible material and can be molded from the same material as stem 56 and/or flange 58. Lip seal 76 can be separately attached to tubular stem 56 in the same manner as previously discussed with regard to flange 58 but is more commonly integrally formed with stem 56 and flange 58. As such, tube port 33 is typically molded as a unitary integral member. In an alternative embodiment, it is appreciated that lip seal 76 can be eliminated from tube port 33 where tube port 33 is not being used to receive a probe or other structure.

In one embodiment, tube port 33 is molded from a soft, resiliently flexible polymeric material or elastomeric material such as polyethylene, silicone or KRATON® having a durometer on a Shore A scale with a value of less than 90 and more preferably less than 70 but typically greater than 5. In other embodiments, other thermoset or thermoplastic polymers having a durometer in the above range can also be used. Other materials such as those previously discussed with regard to container 32 can also be used. In some embodiments, as a result of the material properties, tubular stem 56 can be manually folded over so as to kink passage 68 closed or tubular stem 56 can be manually pinched, such as by a clamp, to close passage 68 wherein in each case tubular stem 56 will resiliently return to the original configuration with substantially no permanent deformation.

In one embodiment, flange 58 has a maximum diameter typically in a range between about 2 cm to about 30 cm with about 5 cm to about 15 cm being more common. Stem 56 typically has a length in a range between about 2 cm to about 30 cm with about 5 cm to about 15 cm being more common. Likewise, stem 56 typically has a maximum inner diameter in a range between about 0.2 cm to about 5 cm with about 0.5 cm to about 3 cm being more common. In alternative embodiments, it is appreciated that each of the above dimensions can be varied. For example, if desired stem 56 can comprise an elongated tube having a length of one meter or longer. It is further noted that in the present embodiment second end 66 of tubular stem 56 has a smooth, substantially cylindrical configuration on interior surface 60 and exterior surface 62 with no flanges, barbs, or other projections extending therefrom.

One of the benefits of tube port 33 is that it is more easily adaptable for coupling with tubes of different diameter or configuration. For example, it is envisioned that container system 30, which comprises container 32 and tube port 33, could be sold to an end user as a single unit. In turn, the established system of the end user may have a variety of different sizes or types of hoses that would connect with stem 56 of tube port 33 for delivering gas, liquid, or other material thereto or for retrieving material from the container. As a result of flexible stem 56, only a single coupler having opposing ends with predefined sizes would be needed to couple stem 56 to the hose.

Figure 5:
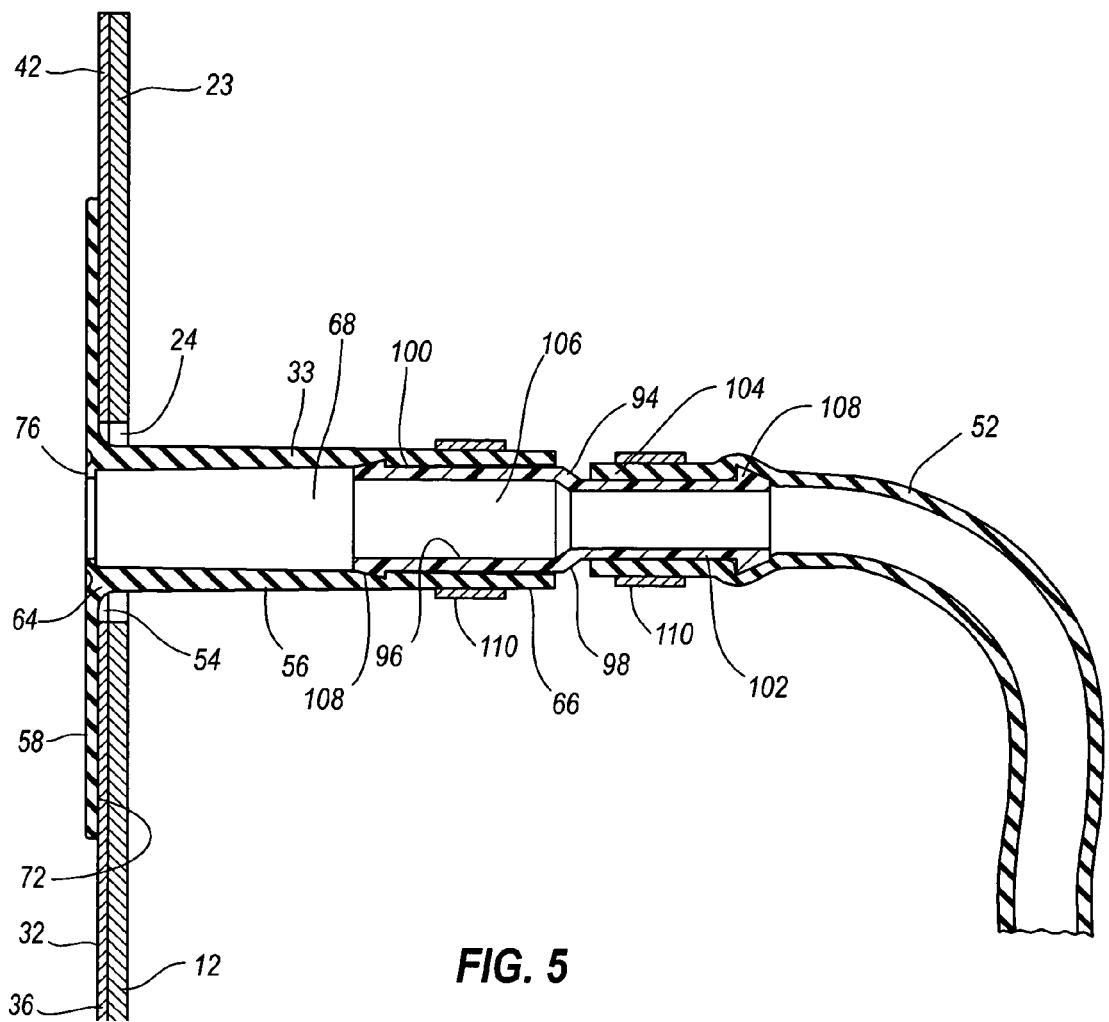
FIG. 5 is a cross sectional side view of the tube port shown in FIG. 2 connected to a fluid line via a connector.

For example, turning to FIG. 5, a tubular connector 94 is provided having an interior surface 96 and an opposing exterior surface 98 each extending between a first end 100 and a longitudinally spaced apart second end 102. Interior surface 96 bounds a passage 106 that longitudinally extends through connector 94. Ends 100 and 102 both have annular barbs 108 radially outwardly projecting therefrom. First end 100 is secured within passage 68 at second end 66 of tubular stem 56. Tubular stem 56 resiliently constricts around connector 94 to form a fluid tight seal therewith. A plastic pull tie 110 can also be secured around the portion of second end 66 of tubular stem 56 disposed over connector 94 so as to further secure the sealed engagement therebetween. Second end 102 of connector 94 is received within a first end 104 of a fluid line 52.

In some embodiments, fluid line 52 has the same diameter as stem 56. In these embodiments, both ends of connector 94 are of equal diameter to each other. If, however, fluid line 52 has a diameter different than stem 56, a standard connector 94 can be provided with second end 102 having a different size than first end 100. Second end 102 is configured to couple with fluid line 52, as shown in the embodiment depicted.

In contrast, if a conventional rigid barbed stem were formed on flange 58, it would be necessary to first couple a tube to the barbed stem and then use connector 94 to account for the change in size of fluid line 52. As a result, stem 56 provides for a more universal connection. Furthermore, as a result of flange 58 and stem 56 both being comprised of a soft and flexible material, container 32 can be folded and/or rolled up for transport and/or storage without fear of damage to tube ports 33 and/or container 32.

Figure 6:
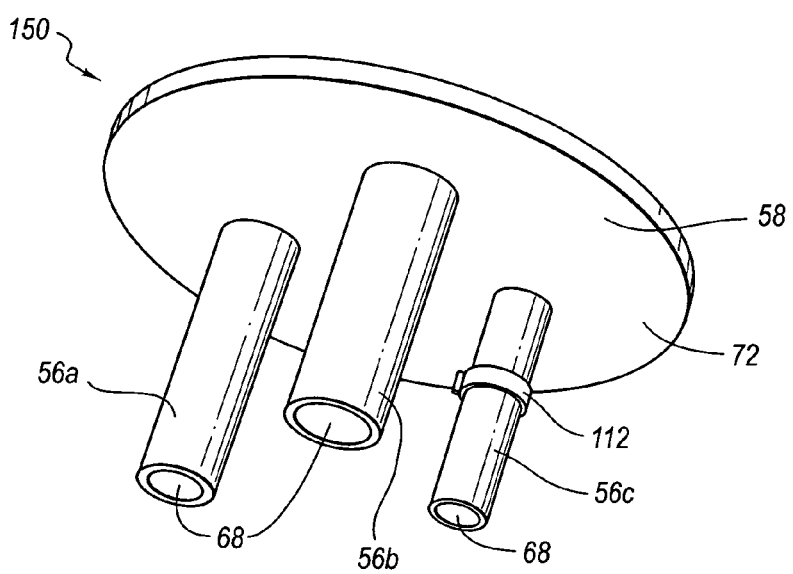
FIG. 6 is a perspective view of an alternative embodiment of a tube port having a plurality of tubular stems.

Depicted in FIG. 6 is a tube port 150 according to an alternative embodiment of the current invention wherein like elements between tube ports 33 and 150 are identified by like reference characters. Tube port 150 comprises a plurality of tubular stems 56a-c projecting from second side 72 of flange 58. Each stem 56a-c has a passage 68 extending longitudinally therethrough and being connected to flange 58 as described above with reference to tube port 33. Although three stems 56a-c are shown, it is appreciated that two, or four or more stems can alternatively be used with the same flange. Each stem 56a-c can be of the same diameter or length as the other stems or all the stems can be sized differently from each other or some combination thereof. One of the benefits of having multiple tubular stems on tube port 150 is that it allows different sizes of connectors 118 to be used when connecting with various fluid lines 52. When a stem is not in use, a clamp 112 can be removably closed across the stem so as to seal closed the passage extending therethrough. It is appreciated that clamp 112 can comprise a hose clamp or a variety of other types of clamps.

Returning to FIG. 1, mounted on side wall 42 is a sampling port 200 which is in fluid communication with chamber 40. Although only one sampling port 200 is shown, it is appreciated that two or more sampling ports 200 can be present depending on the intended use of container 32. As such, each sampling port 200 can serve a different purpose depending on the type of processing to be undertaken. For example, each sampling port 200 can be coupled with an external container (see, e.g., FIG. 9) to deposit fluid or other material withdrawn from chamber 40 or to retrieve fluid or other material to insert into chamber 40. In addition, such as when container 32 is used as a bioreactor for growing cells or microorganisms, sampling ports 200 can simultaneously be used to provide various probes, such as temperature probes, and the like, access to chamber 40 without being contaminated by the material within chamber 40. In one embodiment, sampling port 200 comprises an elongated flexible support tube 202 and an elongated flexible sampling tube 204 each coupled to a body 206, with a flange 208 encircling and radially outwardly projecting from body 206.

Figure 7:
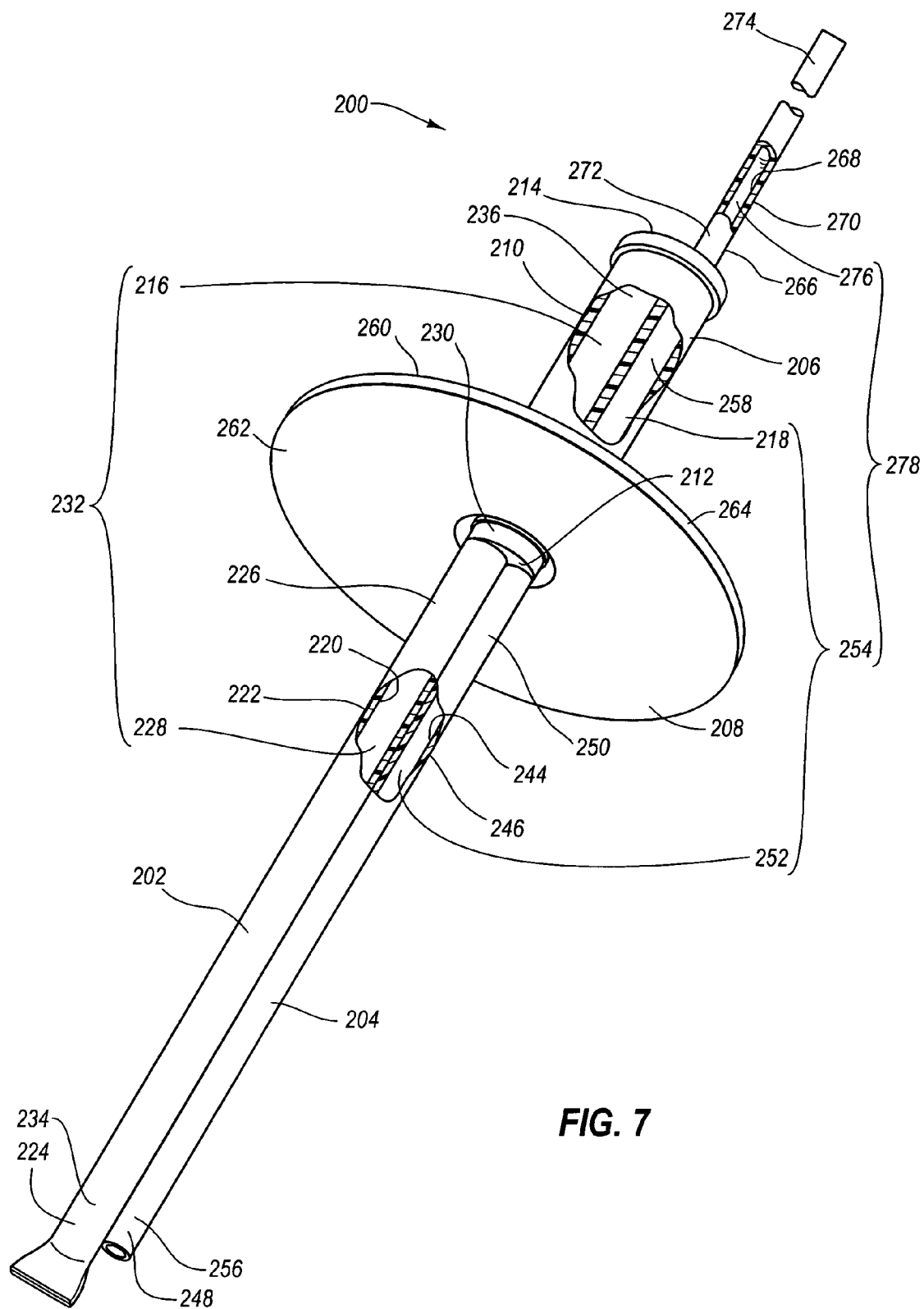
FIG. 7 is a perspective view of the sampling port of the containment system depicted in FIG. 1.

Turning to FIG. 7, body 206 of sampling port 200 has a generally cylindrical shape with an exterior surface 210 extending between a first end face 212 and an opposing second end face 214. Body 206 bounds a first passage 216 and a second passage 218 each extending between first end face 212 and second end face 214. In one embodiment, first passage 216 and second passage 218 extend in adjacent parallel alignment with each other substantially the full length of body 206. In alternative embodiments, exterior surface 210 of body 206 can have a variety of alternative transverse cross sections such as elliptical or polygonal, or irregular.

Support tube 202 of sampling port 200 has an interior surface 220 and an opposing exterior surface 222 each extending between a first end 224 and a longitudinally spaced apart second end 226. Interior surface 220 bounds a first passageway 228 that longitudinally extends through support tube 202. First passageway 228 is open at second end 226 and closed at first end 224. Closure of first end 224 can occur during production or post production by heat sealing, clamping, or any other available method.

Second end 226 of support tube 202 is coupled with first end face 212 of body 206 at a mounting location 230 so as to communicate with first passage 216 of body 206. In this manner, first passageway 228 of support tube 202 and first passage 216 of body 206 combine to form a first continuous passage 232 having a first end 234 at sealed first end 224 of support tube 202 and a second end 236 at open second end face 214 of body 206.

Figure 8:
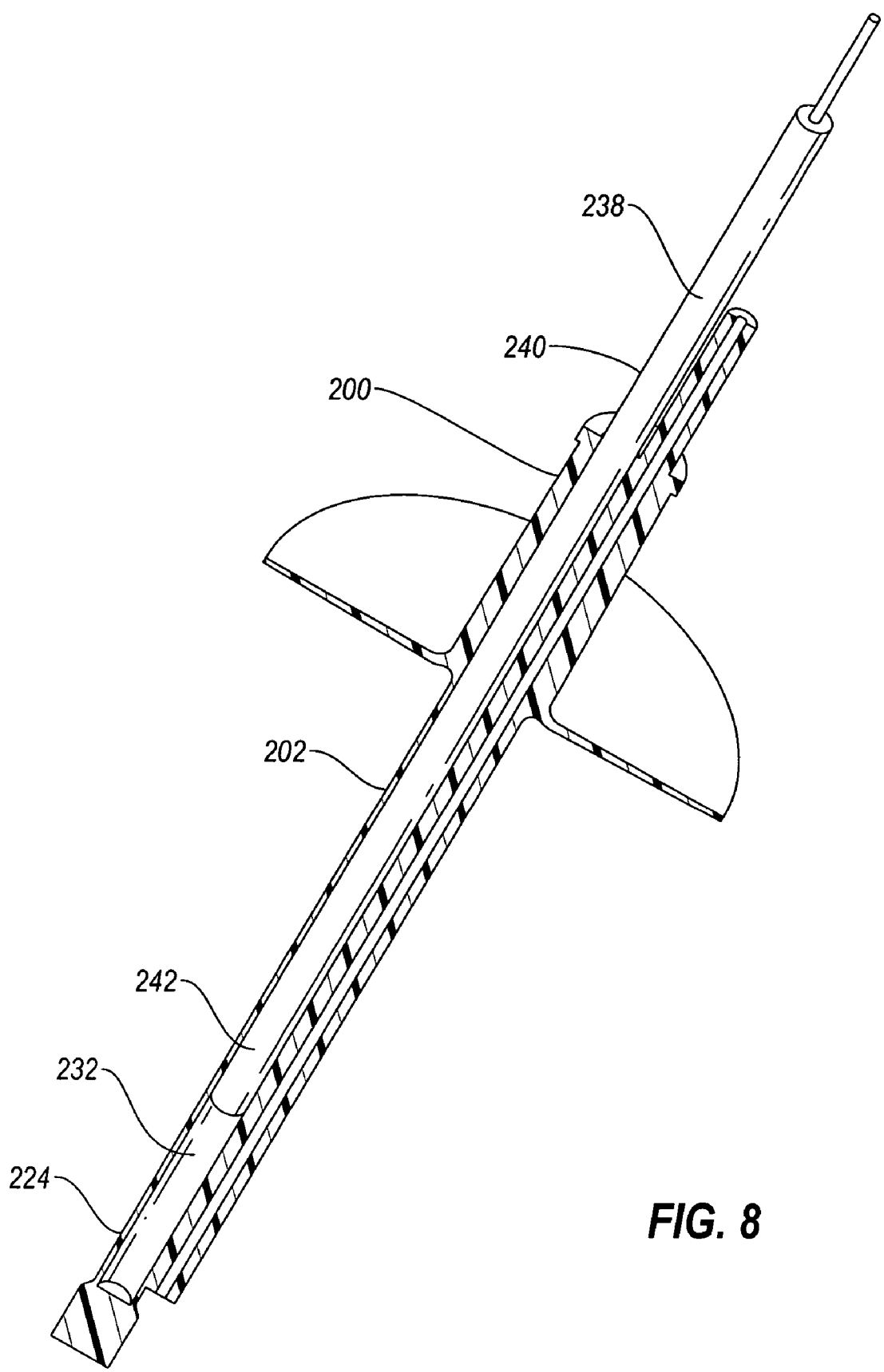
FIG. 8 is a cross sectional side view of the sampling port shown in FIG. 7, with a temperature probe partially inserted therein.

In many embodiments, a probe or other rigid support can be inserted into first continuous passage 232. For example, as shown in FIG. 8, a temperature probe 238 having an exterior surface 240 has been partially inserted into first continuous passage 232 of sampling port 200. When fully inserted, a distal end 242 of temperature probe 238 is disposed at or near sealed first end 224 of support tube 202, which extends into chamber 40 of container 32. When a probe or rigid support is inserted, flexible support tube 202 becomes substantially rigid as it extends into chamber 40 of container 32 as a result of the rigidity of the inserted item.

Because support tube 202 is sealed closed at first end 224, any probe or other support inserted into support tube 202 does not directly contact the liquid or other material within chamber 40 of container 32. As a result, probes or other rigid supports can be inserted and extracted from first continuous passage 232 without fear of any liquid or other material leaking out of chamber 40 or becoming contaminated by probe 238. Furthermore, because probe 238 does not contact the contents of chamber 40, probe 238 can be repeatedly used without the need for sterilization or cleaning between uses.

Returning to FIG. 7, Similar to support tube 202, sampling tube 204 of sampling port 200 has an interior surface 244 and an opposing exterior surface 246 each extending between a first end 248 and a longitudinally spaced apart second end 250. Interior surface 244 bounds a second passageway 252 that longitudinally extends through sampling tube 204. Second passageway 252 is open at second end 250 and, unlike first passageway 228, open at first end 248, thus allowing fluid communication completely through sampling tube 204. Second end 250 of sampling tube 204 is coupled with first end face 212 of body 206 at mounting location 230 so as to communicate with second passage 218 of body 206. In this manner, second passageway 252 of sampling tube 204 and second passage 218 of body 206 combine to form a second continuous passage 254 having a first end 256 at open first end 248 of sampling tube 204 and a second end 258 at open second end face 214 of body 206, allowing fluid communication therethrough.

At least a portion of sampling tube 204 extends along support tube 202 in adjacent parallel alignment with first end 248 of sampling tube 204 being disposed at or toward first end 224 of support tube 202. In the embodiment depicted, sampling tube 204 is in adjacent parallel alignment with support tube 202 along the entire length of sampling tube 204. To facilitate a parallel alignment, sampling tube 204 is coupled with support tube 202 along the entire length of sampling tube 204. In alternative embodiments, sampling tube 204 can be coupled to support tube 202 at spaced apart locations. As a result of this coupling, when a rigid probe or support is inserted into support tube 202, as described previously, sampling tube 204 also becomes substantially rigid as it extends into chamber 40 of container 32.

In the embodiment depicted, sampling tube 204 is of a smaller diameter than support tube 202. It is appreciated that in alternative embodiments, sampling tube 204 can have a larger diameter than or have the same diameter as support tube 202. Sampling tube 204 and support tube 202 each have a length in a range typically between about 2 cm to about 40 cm with about 5 cm to about 25 cm being more common. Other lengths can also be used.

Flange 208 encircles body 206 at mounting location 230 and radially outwardly projects therefrom. In the embodiment depicted, flange 208 has a substantially circular configuration. In alternative embodiments, flange 208 can be any other desired shape such as elliptical, square, or other polygonal or irregular configurations. Flange 208 has a first side 260 and an opposing second side 262 that each extend out to a perimeter edge 264. Support tube 202, sampling tube 204, body 206, and flange 208 can be molded as a unitary integral piece. Alternatively, support tube 202 and sampling tube 204 can be connected to each other and/or to body 206 by welding using conventional welding techniques such as heat welding, RF energy, ultrasonic, and the like or by using adhesives other any other conventional attaching or fastening techniques.

In some embodiments, an elongated collection tube 266 extends outward from second end face 214 of body 206. Collection tube 266 has an interior surface 268 and an opposing exterior surface 270 each extending between a first end 272 and a longitudinally spaced apart second end 274. Interior surface 268 bounds a third passageway 276 that longitudinally extends through collection tube 266. Third passageway 276 is open at first end 272 and second end 274, thus allowing fluid communication completely through collection tube 266. First end 272 of collection tube 266 is coupled with second end face 214 of body 206 so as to communicate with second passage 218. Thus, because second passageway 252 and second passage 218 are in fluid communication with each other as described previously, second passageway 252 of sampling tube 204, second passage 218 of body 206, and third passageway 276 of collection tube 266 combine to form a third continuous passage 278 through which fluid can flow between first end 248 of sampling tube 204 to second end 274 of collection tube 266 in either direction. And because first end 248 of sampling tube 204 and second end 274 of collection tube 266 are both open, fluid can flow externally of third continuous passage 278.

Figure 9:
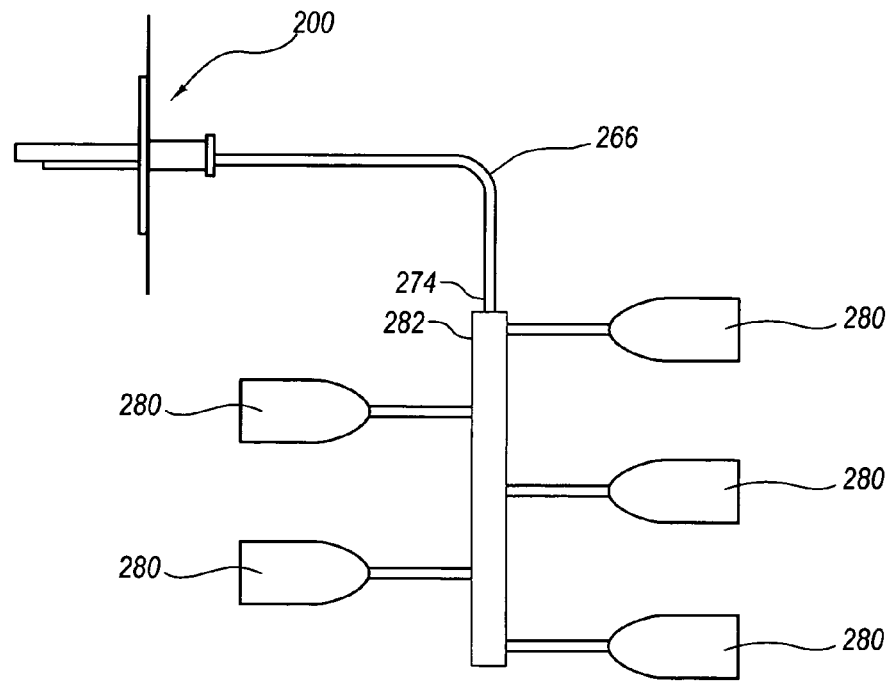
FIG. 9 is a side view of the sampling port shown in FIG. 7, connected to a plurality of collection containers via a collection tube and a manifold.

Turning to FIG. 9, in many embodiments, second end 274 of collection tube 266 is attached to one or more collection containers 280 to store fluid or other material that has been collected from within chamber 40 of container 32. Alternatively, collection tube 266 can be used to retrieve fluid or other material from collection containers 280 to insert into chamber 40. Although the embodiment depicted displays collection tube 266 connected to a manifold 282, which is connected to a plurality of collection containers 280, it is appreciated that collection tube 266 can be attached directly to a single collection container 280, bypassing manifold 282. Collection containers 280 can be any standard containers known in the art for use in such systems but typically comprise sterile plastic bags.

In one embodiment, sampling port 200 is molded from a soft, resiliently flexible polymeric material or elastomeric material such as polyethylene, silicone or KRATON® having a durometer on a Shore A scale with a value of less than 90 and more preferably less than 70 but typically greater than 5. In other embodiments, other thermoset or thermoplastic polymers having a durometer in the above range can also be used. Other materials such as those previously discussed with regard to container 32 can also be used. In some embodiments, as a result of the material properties, support tube 202 and sampling tube 204 can be manually folded over so as to kink the passages therein closed or support tube 202 and sampling tube 204 can be manually pinched, such as by a clamp, to close the passages therein without significant permanent deformation to support tube 202 or sampling tube 204.

Figure 10:
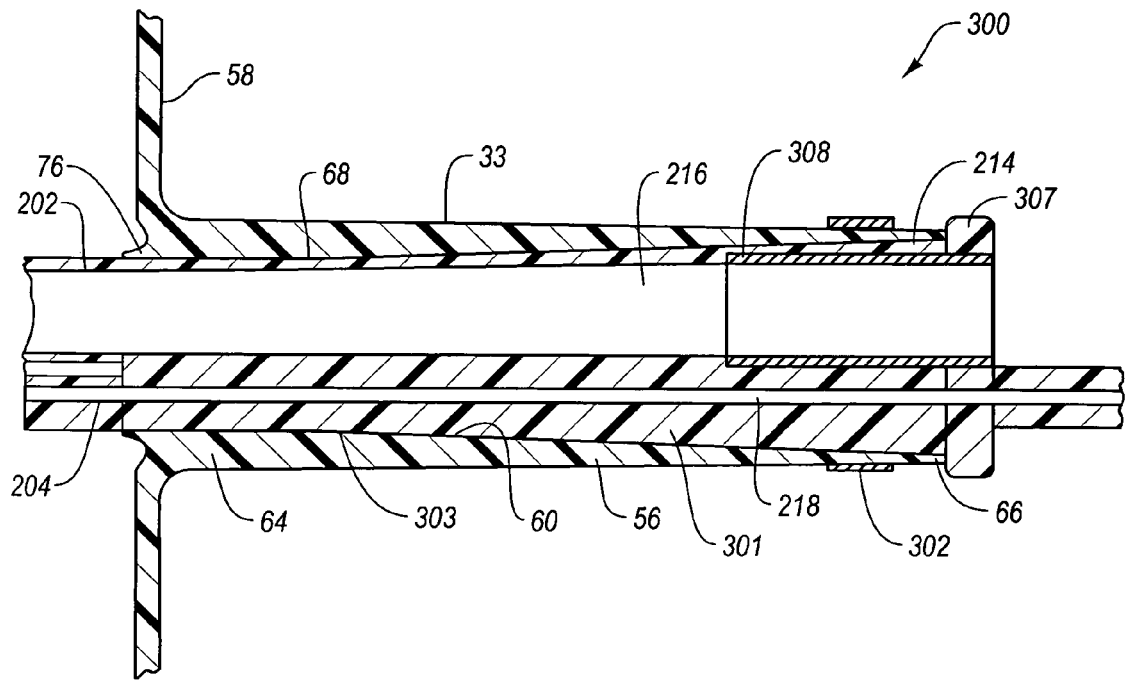
FIG. 10 is a cross sectional side view of a portion of an alternative embodiment of a sampling port.
Figure 11:
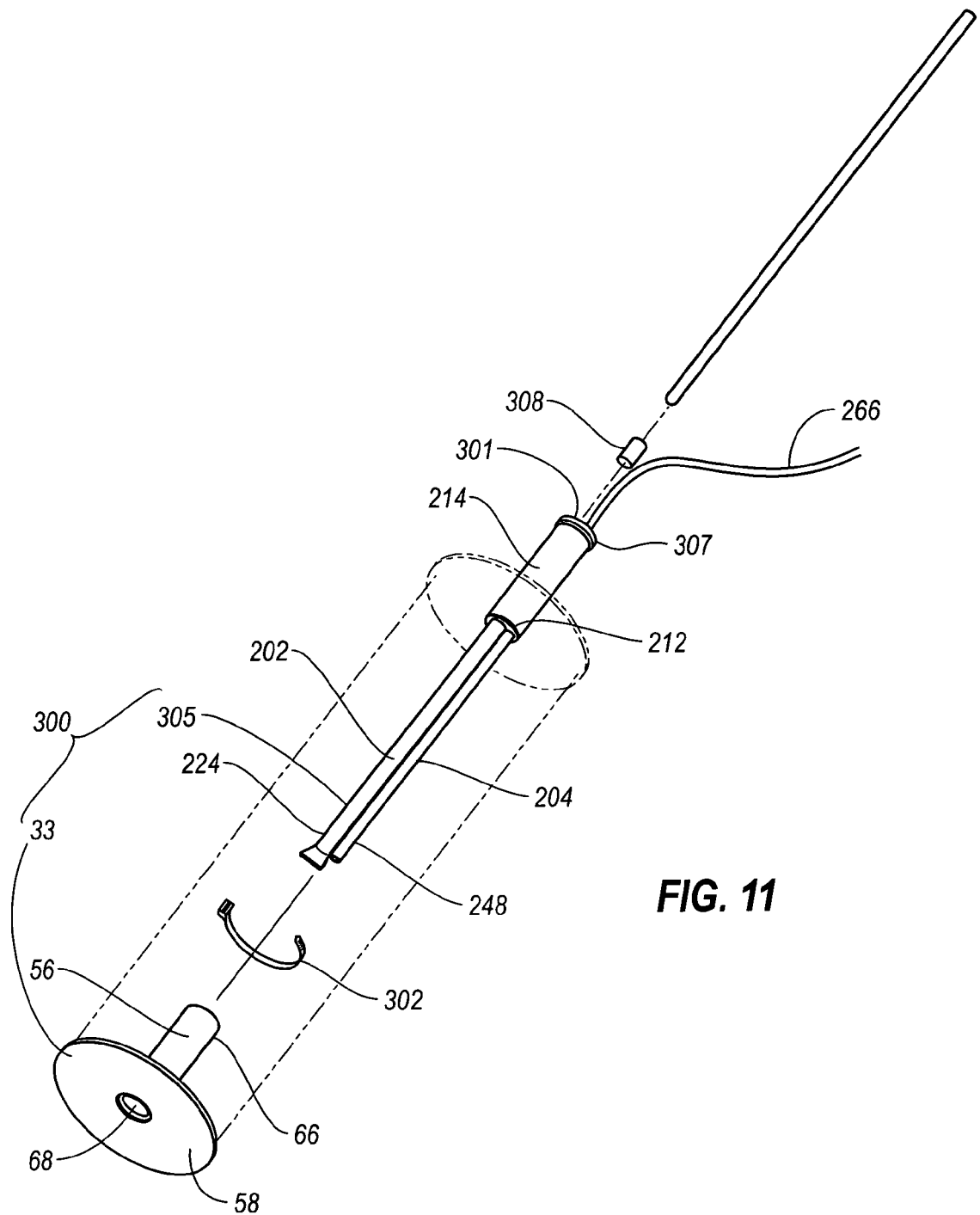
FIG. 11 is an exploded perspective view of the sampling port shown in FIG. 10.

As described previously, in many embodiments support tube 202, sampling tube 204, flange 208, and body 206 are all molded to be a single unitary integral piece. However, it is appreciated that all or some of the elements of the sampling port can alternatively be discrete components that are connected, attached, or otherwise biased together to form the sampling port. For example, depicted in FIGS. 10 and 11 is an alternative embodiment of a sampling port 300 wherein common features between sampling port 200 and sampling port 300 are identified by like reference characters. With reference to FIG. 11, sampling port 300 comprises a tube assembly 305 and tube port 33 as previously discuss.

Tube assembly 305 includes a substantially cylindrical body 301 that is substantially the same as body 206 except that body 301 is sized and shaped to snugly fit within stem 56 of tube port 33. For example, in the embodiment depicted, body 301 has a taper extending along the entire length of body 301 that substantially matches a taper of interior surface 60 of stem 56. Support tube 202 and sampling tube 204 project from first end face 212 of body 301 while collection tube 266 projects from second end face 214 of body 301.

During assembly, support tube 202 and sampling tube 204 are advanced through stem 56 of tube port 33. Tube port 33 is advanced over body 301 until second end 66 butts against an annular shoulder 307 outwardly projecting from the second end of body 301. As depicted in FIG. 10, in this position lip seal 76 radially biases against exterior surface 303 of body 301 at the first end thereof so as to form a sealed engagement therebetween. To provide a more secure engagement and seal between stem 56 and body 301, one or more pull ties, clamps, or other tightening devices can be used. For example, in the embodiment depicted a plastic pull tie 302 is secured around the portion of second end 66 of tubular stem 56 disposed over body 301 so as to further secure the sealed engagement therebetween.

To keep one or both of passages 216 or 218 from collapsing under the force of pull tie 302, a rigid sleeve 308 made of metal or other rigid material can be inserted into first passage 216 prior to tightening pull tie 302. Pull tie 302 is positioned so as to be disposed over sleeve 308. Sleeve 308 is disposed within first passage 216 because first passage 216 has a larger diameter than second passage 218 and thus can more easily collapse. Where the diameter of second passage 218 is increased, a second rigid sleeve 308 can also be positioned therein. It is appreciated that other types of tightening devices can be used alternatively or in conjunction with pull tie 302. After pull tie 302 is positioned, the assembled sampling port 300 can be secured to container 32 by welding flange 58 to container 32 using conventional welding techniques. The entire assembly can then be sterilized using radiation or other types of sterilization. During use, temperature probe 238 or other rigid device can then be inserted into support tube 202, if desired.

It is appreciated that the sampling ports can come in a variety of other alternative configurations. For example, depicted in FIG. 12 is an alternative embodiment of a sampling port 320 incorporating features of the present invention. Common features between sampling port 200 and sampling port 320 are identified by like reference characters. For example, sampling port 320 comprises an elongated flexible support tube 202, an elongated flexible sampling tube 204, and a flange 208. However, in contrast to sampling port 200, sampling port 320 does not have a body. Instead, flange 208 simply encircles and radially outwardly projects from support tube 202 and sampling tube 204 at a mounting location 322. Support tube 202 and sampling tube 204 can be coupled together at discrete locations or along their entire length. If a collection tube is used, collection tube 266 extends outward from second end 250 of sampling tube 204 at mounting location 322 such that third passageway 276 of collection tube 266 fluidly communicates with second passageway 252 of sampling tube 204.

Depicted in FIGS. 13A-B is another alternative embodiment of a sampling port 330 incorporating features of the present invention. Like elements between sampling port 200 and sampling port 330 are identified by like reference characters. Instead of having discrete support and sampling tubes as in sampling port 200, sampling port 330 has an elongated flexible member 332 having two separate passages enclosed therein. Flexible member 332 has an exterior surface 334 extending between a first end 336 and an opposing second end 338. Member 332 bounds a first passageway 340 and a second passageway 342 each extending between first end 336 and second end 338. Similar to first passageway 228 of support tube 202 of sampling port 200, first passageway 340 of sampling port 330 is open at second end 338 and closed at first end 336. Similar to second passageway 252 of sampling tube 204 of sampling port 200, second passageway 342 of sampling port 330 is open at first end 336 and second end 338. Although not depicted as such, sampling port 330 may also include a body 206 similar to sampling port 200.

If a collection tube is used, collection tube 266 extends outward from second end 338 of member 332 such that third passageway 276 of collection tube 266 fluidly communicates with second passageway 342 of member 332. Of course, as with all embodiments having a collection tube, the second end 274 of collection tube 266 can be connected to one or more collection containers 280, as previously discussed.

First passageway 340 and second passageway 342 can have a number of different configurations. For example, in the embodiment depicted, first passageway 340 and second passageway 342 are in adjacent parallel alignment with each other. Alternatively, as shown in FIGS. 14A-B, second passageway 342 can radially encircle first passageway 340 at first end 336 of flexible member 332, but not necessarily encircle first passageway 340 at second end 338. It is appreciated that many other configurations are also possible. Regardless of the configuration, in the depicted embodiments first passageway 340 is closed at first end 336 and second passageway 342 is open at first end 336. It is also desirable for first passageway 340 to be able to be aligned in a straight line so as to accommodate a rigid temperature probe or the like.

Figure 15:
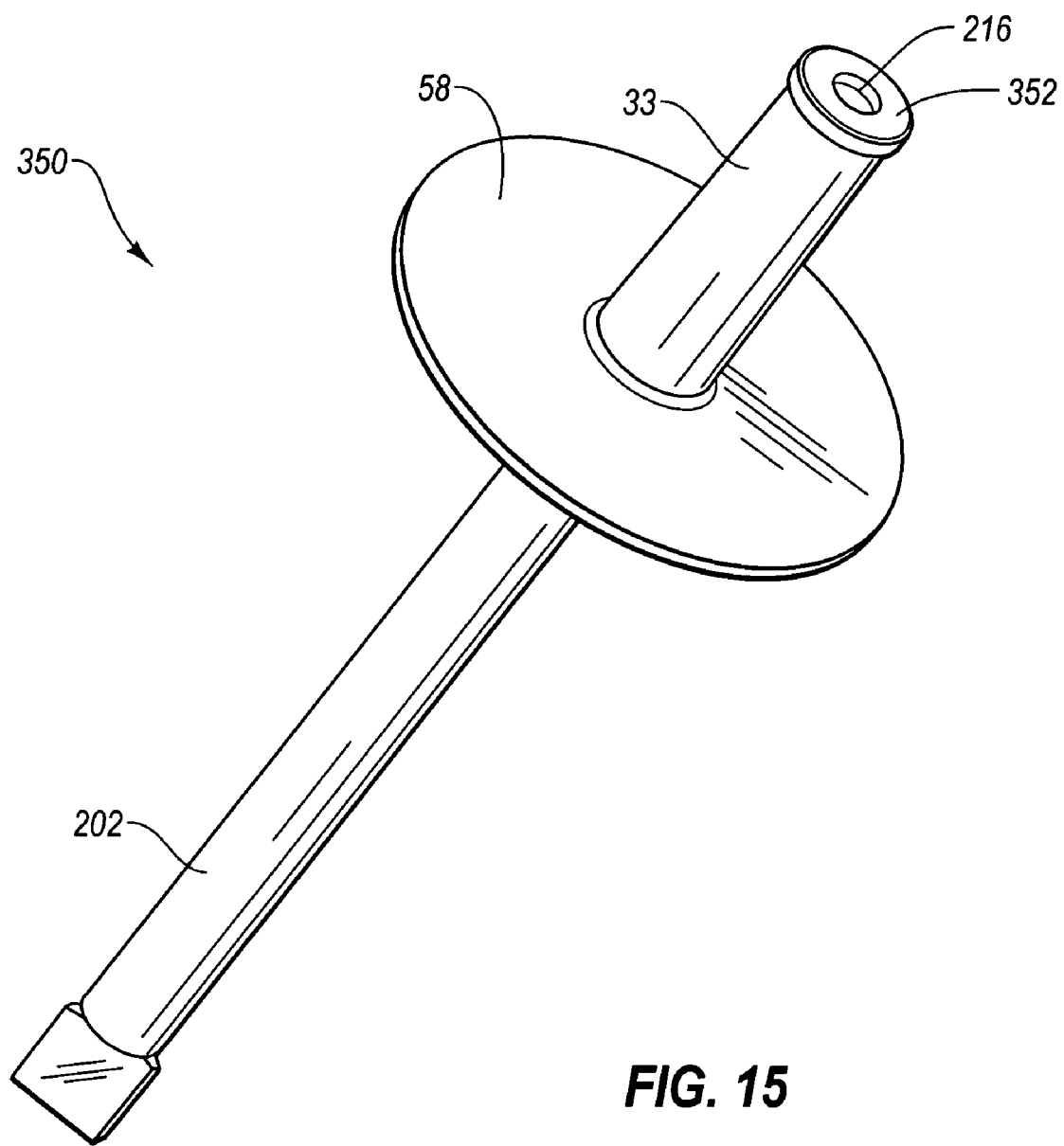
FIG. 15 is a cross sectional side view of yet another alternative embodiment of a sampling port containing no sampling tube.

Depicted in FIG. 15 is one embodiment of a probe port 350 using tube port 33 and incorporating features of the present invention. Like elements between sampling port 300 and probe port 350 are identified by like reference characters. Probe port 350 comprises a body 352 that is similar to body 301 (FIG. 10) except that second passage 218 has been removed. Support tube 202 connects to and projects from body 352 so as to communicate with first passage 216. Tube port 33 couples with body 352 in the same manner that tube port 33 coupled with body 301. In this embodiment, a probe, such as a temperature probe, can be inserted into support tube 202 of probe port 350 to monitor conditions within chamber 40 without the probe being contaminated by any material within chamber 40. However, unlike sampling port 300, no sampling of material from within chamber 40 can be performed using probe port 350.

It is appreciated that the various sampling ports have many of the same advantages as previously discussed with regard to the tube port. For the sampling ports are inexpensive to manufacture, disposable, scalable, and can be rolled up and folded within container 32 during manufacture, sterilization, storage and transport without risk of damage to container 32 or the sampling port. Other advantages have been discussed herein or are readily apparent from the design.

Returning to FIGS. 1 and 5, extending through side wall 42 of container 32 are a number of holes 54. Each hole 54 is aligned with a corresponding opening 24 on sidewall 23 of support housing 12. A portion of a tube port 33 or a sampling port 200 according to various embodiments of the present invention extends through each one of the holes 54 and openings 24. Each tube port 33 or sampling port 200 is sealed to body 36 of container 32 so that fluid cannot leak out through hole 54.

For each tube port 33, second surface 72 of flange 58 is sealed to sidewall 42 of container 32 so as to secure tube port 33 to container 32 and to prevent liquid or other material from leaking out through hole 54. Flange 58 is typically secured to container 32 by conventional welding techniques. Alternatively, however, adhesives or mechanical connections can also be used.

Similar to flange 58 of each tube port 33, first side 260 of flange 208 is sealed to sidewall 42 of container 32 for each sampling port 200 so as to secure sampling port 200 to container 32 and to prevent liquid or other material from leaking out through hole 54. Flange 208 is typically secured to container 32 by conventional welding techniques. Alternatively, however, adhesives or mechanical connections can also be used. If a tube port 33 is used in conjunction with a sampling port (see, e.g., sampling port 300 of FIGS. 10 and 11), flange 58 of tube port 33 is sealed to sidewall 23 as described previously, then body 301 and/or support and sampling tubes 202 and 204 are inserted through passage 68 of stem 56 until exterior surface 303 of body 301 biases against interior surface 60 of tubular stem 56, creating a liquid tight seal. It is appreciated that flange 58 alternatively can be sealed to sidewall 42 after body 301 has been inserted through passage 68.

Once container system 30 is fully assembled, the system can be sealed within a storage bag and the entire system sterilized such as through various forms of radiation sterilization.

During operation, container system 30 is positioned within compartment 20 of support housing 12 so that stems 56 of tube ports 33 and bodies 206 and/or support and sampling tubes 202 and 204 of sampling ports 200 pass through openings 24 in support housing 12.

For each tube port 33, a tube, such as fluid line 52, is then coupled with stem 56 using connector 118 as previously discussed, or a probe 84, such as temperature probe, a dissolved oxygen probe, or the like, is inserted through stem 56 into chamber 40 of container 32, so that a substantially liquid tight seal is formed between an exterior surface of connector 118 or probe 84 and stem 56.

Next, a fluid 41 is dispensed into chamber 40 of container 32 by way of ports 33 which are coupled to input fluid lines 52. Fluid 41 can comprise a variety of different materials. For example, where container system 30 is being used as a bioreactor for growing cells or microorganisms, fluid 41 can comprise a growth media that is dependent upon the type of cells or microorganism being cultured. The fluid can also include a seed inoculum such as bacteria, fungi, algae, plant cells, animal cells, protozoans, nematodes, or the like. The present invention can also be used for non-biological systems. For example, the system can be used for processing or mixing solutions where it is desired to control or regulate the pH or partial pressure of gas within a solution. The fluid is prevented from leaking out of chamber 40 by way of the substantially liquid tight seals formed between connectors 118 or probes 84 and stems 56, as discussed previously.

For each sampling port 200, a probe, such as temperature probe 238 or other type of rigid support, is inserted into first continuous passage 232 of sampling port 200, as discussed previously. Because support tube 202 is sealed closed at first end 224, probes or other types of rigid supports can be inserted and extracted using sampling port 200 while liquid or other material remains within chamber 40 while preventing any material to leak out of chamber 40.

Various parameters within chamber 40 of container 32 are measured by the probes that have been inserted into chamber 40 using tube ports 33 and sampling ports 200. These parameters can include temperature, pressure levels, and the like and can be measured once, periodically, continuously, or in any other known manner.

When desired, material is removed from chamber 40 of container 32 using sampling tubes 204 of sampling ports 200 which are coupled to collection tubes 266. When a rigid support or probe has been inserted into support tube 202, the rigid probe or support allows sampling tube 204 to extend relatively rigidly into chamber 40 due to the coupling between support tube 202 and sampling tube 204, discussed previously. This allows sampling tube 204 to retrieve the sample from deeper within chamber 40, further away from the interior surface 38 of container 32 than would be allowed otherwise. This gives a more representative sample of the material within chamber 40. Once retrieved, the material is then deposited in one or more collection containers 280 for further processing, as discussed previously.

As previously mentioned, the illustrative container system 10 depicted in FIG. 1 is generally configured as a bioreactor for growing cells or microorganism. To that end, a sparger 34 is mounted on container 32 for delivering controlled gases to growth media that is disposed within container 32. Further disclosure with regard to sparger 34 is disclosed in U.S. patent application Ser. No. 11/112,834 that was previously incorporated herein by specific reference and a United States patent application entitled Gas Spargers and Related Container Systems in the names of Michael E. Goodwin, Nephi D. Jones, Jeremy K. Larsen filed Mar. 20, 2006 which is incorporated herein by specific reference.

In one embodiment it is noted that sparger 34 can be formed by securing a gas permeable sparger material to flange 58 of tube port 33 so that by delivering a gas though stem 56, the gas is forced to travel out through the gas permeable sparger material. Further disclosure with regard to the types of materials that can be used for the gas permeable sparger material and how to attach it to flange 58 are also disclosed in the above referenced patent application entitled Gas Spargers and Related Container Systems.

Although not required, in one embodiment means are also provided for mixing fluid within chamber 40. By way of example and not by limitation, in one embodiment a drive shaft 114 projects into chamber 40 and has an impeller 116 mounted on the end thereof. External rotation of drive shaft 114 thus facilitates rotation of impeller 116 which mixes and/or suspends fluid within chamber 40. Sparger 34 is typically disposed directly below the means for mixing such that the mixing or movement of the fluid produced by the mixer helps to entrain the gas bubbles within the fluid. One specific example of how to incorporate a rotational mixer into a flexible container is disclosed in U.S. Patent Publication No. US 2005/0239199 A1 published Oct. 27, 2005 which is incorporated herein by specific reference. Another example is disclosed in United States Provisional Patent Application filed Mar. 20, 2006, entitled Mixing Systems and Related Mixers in the names of Whitt F. Woods et al. which is incorporated herein by specific reference.

In an alternative embodiment of the means for mixing, mixing can be accomplished by vertically reciprocally moving a vertical mixer within chamber 40. Further disclosure with regard to the assembly and operation of a vertical mixer is disclosed in U.S. patent application Ser. No. 11/127,651, filed May 11, 2005 which is incorporated herein by specific reference. In yet other embodiments, it is appreciated that the mixing can be accomplished by simply circulating fluid through chamber 40 such as by using a peristaltic pump to move fluid in and out of chamber 40. Other conventional mixing techniques can also be used.

It is appreciated that the foregoing embodiments are simply examples of alternative methods of forming tube ports or sampling ports of the present invention. It is likewise appreciated that the various features of the different embodiments can be mixed and matched to produce still other embodiments.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sampling port comprising:
   an elongated flexible support tube having an interior surface bounding a first passageway extending between a first end and an opposing second end, the first passageway being closed at the first end of the support tube and open at the second end of the support tube;

an elongated flexible sampling tube having an interior surface bounding a second passageway extending between a first end and an opposing second end, the second passageway being open at the first end of the sampling tube, at least a portion of the sampling tube adjacently extending along the length of the support tube and being connected to the support tube; and a flange encircling and radially outwardly projecting from the support tube and the sampling tube at a location spaced apart from the first end of the support tube and the first end of the sampling tube.

2. The sampling port as recited in claim 1, wherein substantially the full length of the sampling tube or the support tube extending between the flange and the first end thereof extends in adjacent parallel alignment with the other of the sampling tube or support tube.

3. The sampling port as recited in claim 1, wherein the first end of the support tube is heat sealed closed.

4. The sampling port as recited in claim 1, wherein the support tube, the sampling tube and the flange are integrally molded as a unitary member.

5. The sampling port as recited in claim 1, further comprising:

the support tube and sampling tube being secured together at the location of the flange so as to form a body thereat having an exterior surface with a substantially cylindrical configuration; and a tube port removably coupled with the body, the tube port comprising:

a tubular stem having an interior surface bounding a passage, the body being received within the passage; and the flange encircling and radially outwardly projecting from the tubular stem.

6. The sampling port as recited in claim 5, further comprising an annular lip seal radially inwardly projecting from the interior surface of the tubular stem and biasing against the exterior surface of the body.

7. The sampling port as recited in claim 1, further comprising a sampling container connected to the second end of the sampling tube.

8. The sampling port as recited in claim 1, wherein the support tube, the sampling tube and the flange are each comprised of an elastomeric material having a durometer on a Shore A scale with a value of less than 90.

9. The sampling port as recited in claim 8, wherein the elastomeric material is comprised of polyethylene.

10. The sampling port as recited in claim 1, wherein the sampling tube and the support tube each have a length extending from the flange to their corresponding first end of at least 10 cm.

11. A container system comprising:

a container having an interior surface bounding a chamber, the chamber being adapted to hold a fluid;

the sampling port as recited in claim 1 coupled with the container so that the first end of the support tube and the first end of the sampling tube are both disposed within the chamber of the container; and a substantially rigid support being removably disposed within the first passageway of the support tube.

12. The container system as recited in claim 11, wherein the rigid support comprises a temperature probe.

13. The container system as recited in claim 11, wherein the container comprises a bag that is comprised of one or more sheets of flexible polymeric material.

* * * * *